United States Patent [19]

Brenner et al.

[11] Patent Number: 5,780,455
[45] Date of Patent: Jul. 14, 1998

[54] INTRAVENOUS ALENDRONATE FORMULATIONS

[75] Inventors: Gerald S. Brenner, Norristown; Musa M. Ghannam, Phoenixville, both of Pa.

[73] Assignee: Merck & Co., Inc., Rahway, N.J.

[21] Appl. No.: 296,192

[22] Filed: Aug. 24, 1994

[51] Int. Cl.$^6$ .................................................. A61R 31/66
[52] U.S. Cl. ........................................................ 514/108
[58] Field of Search ................................. 514/77, 108

[56] References Cited

U.S. PATENT DOCUMENTS

| | | |
|---|---|---|
| 4,922,007 | 5/1990 | Kieczykowski et al. |
| 4,927,814 | 5/1990 | Gall .................................................. 514/108 |
| 5,019,651 | 5/1991 | Kieczykowski . |
| 5,462,932 | 10/1995 | Brenner ............................... 514/108 |

OTHER PUBLICATIONS

Remington, Pharmaceutical Sciences, 18th Ed., pp. 1549–1550.
Nussbaum, (J. Clinical Oncology, 11(8), 1619) Aug. 1993.
Averbuch, (Cancer Supplement 72(11), 3444–52) Dec. 1993.
De Marco, et al., J. Pharm. Biomed. Anal. 7(12), 1719–27 1989.
"New Bisphosphonates in the Treatment of Bone Metastases" by Steven D. Averbuch, Cancer Supplement vol. 72, No. 11, Dec. 1, 1993, pp. 3444–3452.
"Dose–Response Study of Alendronate Sodium for the Treatment of Cancer–Associated Hypercalcemia" by S. R. Nussbaum, et al., Journal of Clinical Oncology, vol. 11, No. 8 (Aug.) 1993, pp. 1618–1623.

United States Pharmacopeia/National Formulary for 1995, "General Tests and Assays" Water for Injection, pp. 1636–1637.

United States Pharmacopeia/National Formulary for 1995, "General Tests and Assays" Sterility, pp. 1686–1690.

United States Pharmacopeia/National Formulary for 1995, "General Tests and Assays" Pyrogen, pp. 1718–1719.

United States Pharmacopeia/National Formulary for 1995, "General Tests and Assays" Particulates, pp. 1813–1819.

United States Pharmacopeia/National Formulary for 1995, "General Tests and Assays" Tonicity, p. 1813.

United States Pharmacopeia/National Formulary for 1995, "General Tests and Assays" pH, pp. 1819–1820.

Nussbaum, et al., J. Clinical Oncology, vol. 11, No. 8 (Aug. 1993): pp. 1618–1623.

Physicians' Desk Reference, 1996, pp. 1488 and 810.

Fleisch, H. Bisphosphonates –Pharmacology and Use in the Treatment of Tumour–Induced Hypercalcaemic and Metastatic Bone Disease–Drugs 42(6) 1991 pp. 919–944.

*Primary Examiner*—Robert Gerstl
*Attorney, Agent, or Firm*—Anthony D. Sabatelli; Melvin Winokur

[57] ABSTRACT

Disclosed is a therapy protocol for treating patients having metastatic bone disease, hypercalcemia of malignancy and/or metabolic bone disease by administering an intravenous, citrate-buffered formulation of alendronate which is isotonic with human blood.

3 Claims, No Drawings

1

INTRAVENOUS ALENDRONATE FORMULATIONS

FIELD OF THE INVENTION

The instant invention relates to the use of isotonic intravenous formulations of alendronate, i.e., 4-amino-1-hydroxy-butylidene-1,1-bisphosphonic acid monosodium trihydrate, for the treatment of metastatic bone disease, hypercalcemia of malignancy, and/or metabolic bone disease including osteoporosis and Paget's disease in human patients.

BACKGROUND OF THE INVENTION

Metastatic bone disease involves tumor-induced skeletal metastases which commonly result from breast cancer, prostate cancer, lung cancer, renal cancer, thyroid cancer and multiple myeloma. The prevalence of bone metastases in patients with these cancers may be as high as 60–85%. Patients with these diseases that have bone dominant or bone only metastases frequently have prolonged survival, usually associated with clinical morbidity. The most frequent clinical manifestations of bone metastases are pain, pathological fracture, immobility, nerve root or spinal cord compression, hypercalcemia and compromised hematopoiesis. The scope of metastatic bone disease is highlighted by the fact that on any given day, approximately 4 million people worldwide suffer from cancer pain and that at least 40–50% of all cancer pain is due to skeletal metastases.

Hypercalcemia of malignancy is also tumor-induced. It is characterized by high levels of serum calcium and is often associated with metastatic bone disease, particularly with non-ambulatory patients. It is estimated that hypercalcemia develops in 5% to 10% of hospital cancer patients. Symptoms of hypercalcemia include fatigue, malaise, anorexia, polydipsia, nausea, constipation, muscle weakness, apathy, obtundation and even coma. These metabolic complications of malignancy mostly reflect a disseminated disease. Thus, in the majority of cases, malignancy is recognized before the appearance of hypercalcemia. However, in rare situations, such as neuroendocrine tumors, hypercalcemia may run a slowly developing course and even precede the discovery of the tumor.

The category of metabolic bone disease includes osteoporosis and Paget's disease, in which osteoporosis is one of the most important disorders associated with aging. More than 1.5 million Americans have fractures related to osteoporosis each year, with attendant pain, deformity and loss of independence. The annual cost to the U.S. health care system is at least $10 billion. Because of the aging of the population and increases over time in the incidence of fractures, these already huge costs will more than double over the next 30 years unless a comprehensive program of prevention and treatment is initiated soon. The most important preventable cause of fractures is low bone mass. During the course of their lifetimes, women lose about 50 percent of their cancellous bone and 30 percent of their cortical bone, and men lose about 30 percent and 20 percent, respectively. Cancellous bone is concentrated in the spinal column and at the ends of long bones; these areas are the main sites of osteoporotic fractures. The tendency of the elderly to fall, however, is an important independent cause of fractures. Although little can be done at present to prevent such falls, important advances have been made in methods of retarding bone loss involving the use of bisphosphonates.

Alendronate, 4-amino-1-hydroxybutylidene-,1-bisphosphonic acid monosodium trihydrate, is a new bisphosphonate agent for combatting bone resorption in metabolic bone diseases including osteoporosis and Paget's disease and is described as a composition, method of use and synthesis along with other pharmaceutically acceptable salts in U.S. Pat. Nos. 4,922,007 and 5,019,651 (both assigned to Merck).

Alendronate is also used in treating metastatic bone disease for example, as described in *Cancer* 72, (Supplement) 3443–3452(1993) by S. D. Averbuch. Its use in treating hypercalcemia of malignancy is described in *Journal of Clinical Oncology*, Vol. 11, No 8 (Aug.), 1993, pp. 1618–1623 by S. R. Nussbaum et al.

Alendronate currently is administered orally or intravenously to patients. The advantage of intravenous therapy over oral dosage therapy is that therapeutically higher levels of serum alendronate can be achieved in a relatively short time period. This is especially important in hypercalcemia of malignancy where it is desired to lower serum calcium levels as quickly as possible to minimize calcium deposition and resulting bone disorders.

However, a major problem is that intravenous solutions of alendronate are prepared and packaged in glass containers and tend to form a precipitate during shelf storage. This has shown to be a result of metal ion precipitation of alendronate at increasingly higher pH values forming insoluble metal complexes. Precipitates are very dangerous in an intravenous formulation since they can lead to embolisms and blocking of capillaries which can be fatal. Thus, intravenous formulations for clinical studies and marketing must pass a series of rigid government (United States or international) and compendial tests, including the USP (United States Pharmacopeia in the United States) test for particulate matter. With respect to packaging, the use of glass containers is highly desirable since the formulation contents can be quickly inspected for the presence of particulates, and glass is a very efficient and convenient medium for packaging.

What is desired is a therapeutically effective alendronate intravenous formulation which is solution stable, isotonic with human blood, can be packaged in glass, meets government and compendial (USP in the US) particulate standards, and which can be used as effective therapy to optimally treat patients with metastatic bone disease, hypercalcemia of malignancy and/or metabolic bone disease.

SUMMARY OF THE INVENTION

We have discovered that a sodium citrate/citric acid buffer can maintain the pH of the alendronate intravenous formulation between 4–8 and acts as a complexing agent to maintain metal ions in solution which are leached out of the glass container. Both of these effects, maintaining the lower pH and complexing metal ions by the citrate buffer, prevents metal ions from precipitating alendronate and can maintain the intravenous formulation in an acceptable particulate profile for storage and subsequent use.

By this invention there is provided a pharmaceutical composition comprising a pharmaceutically effective amount of alendronate, in a pharmaceutically acceptable, aqueous carrier for intravenous application and a sufficient amount of a buffer to maintain the pH of the composition in the range of 4 to 8 to prevent the precipitation of alendronate by metal ions in aqueous solution, said composition being isotonic with human blood.

The present invention also provides a method for treating and/or preventing metastatic bone disease, hypercalcemia of malignancy and/or metabolic bone disease in a subject who is in need of same comprising the step of administering to

3 said patient a pharmaceutically effective amount of alendronate, in a stable citrate-buffered, isotonic, intravenous formulation.

DETAILED DESCRIPTION OF THE INVENTION AND PREFERRED EMBODIMENTS

Liquid intravenous solutions of alendronate offer the advantages of ease of administration, increased compliance for ambulatory patients, who have difficulty ingesting solid oral dosage forms, and for hospitalized patients who require therapeutically large doses of alendronate in a short time period.

This method is especially useful for treating metastatic bone disease and hypercalcemia and can also be used for treating patients to inhibit bone resorption in other metabolic bone disorders, e.g., Paget's disease and osteoporosis.

The term "inhibition of bone resorption" as used herein, refers to treatment and prevention of bone loss, especially inhibiting the removal of existing bone either from the mineral phase and/or the organic matrix phase, through direct or indirect alteration of osteoclast formation or activity. Thus, the term "inhibitor of bone resorption" as used herein refers to agents that prevent bone loss by the direct or indirect alteration of osteoclast formation or activity and which may increase bone mass in patient treatment populations.

The term "osteogenically effective" as used herein, means that amount which effects the turnover of mature bone. As used herein, an osteogenically effective dose is also "pharmaceutically effective."

The term "treatment" or "treating" as used herein shall mean (1) providing a subject with an amount of alendronate sufficient to act prophylactically to prevent the development of a weakened and/or unhealthy state; and/or (2) providing a subject with a sufficient amount of alendronate so as to alleviate or eliminate a disease state and/or the symptoms of a disease state, and a weakened and/or unhealthy state.

Pharmaceutical intravenous formulations of the invention will generally include an osteogenically effective amount of alendronate to treat metastatic bone disease and/or hypercalcemia of malignancy and also to inhibit bone resorption, in addition to a pharmaceutically acceptable excipient. The compositions are advantageously prepared together with liquid inert carriers, a useful one being water. Suitable liquid excipients/carriers are Water for Injection (USP in the US) and saline solution.

Other suitable excipients and other accessory additives are as follows:
Solvents
    ethanol
    glycerol
    propylene glycol
Stabilizers
    EDTA (ethylene diamine tetraacetic acid)
    citric acid
Antimicrobial Preservatives
    benzyl alcohol
    methyl paraben
    propyl paraben
Buffering Agents
    citric acid/sodium citrate
    potassium hydrogen tartrate
    sodium hydrogen tartrate
    acetic acid/sodium acetate
    maleic acid/sodium maleate
    sodium hydrogen phthalate
    phosphoric acid/potassium dihydrogen phosphate
    phosphoric acid/disodium hydrogen phosphate
Tonicity Modifiers
    sodium chloride
    mannitol
    dextrose Alendronate is present in an amount of about 0.5 to 10 milligrams/milliliter of the composition and a useful value is 2.5 mg/ml of composition.

In addition, the presence of a buffer is necessary to maintain the aqueous pH in the range of 4–8 and a useful range being 4–6.

The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, phosphoric acid/potassium dihydrogen phosphate, and phosphoric acid/disodium hydrogen phosphate.

The amount of buffer system used is dependent on (1) the desired pH; and (2) the amount of alendronate. Generally, the amount of buffer used is in a 0.5:1 to 50:1 mole ratio of buffer:alendronate (where the moles of buffer are taken as the combined moles of the buffer ingredients, e.g., sodium citrate and citric acid) of formulation to maintain a pH in the range of 4 to 8 and generally, a 1:1 to 10:1 mole ratio of buffer (combined) to alendronate present is used.

A useful buffer in the invention is sodium citrate/citric acid in the range of 5 to 50 mg per ml. sodium citrate to 1 to 15 mg per ml. citric acid, sufficient to maintain an aqueous pH of 4–6 of the composition.

The buffer agent is also present to prevent the precipitation of alendronate through soluble metal complex formation with dissolved metal ions, e.g., Ca, Mg, Fe, Al, Ba, which may leach out of glass containers or rubber stoppers or be present in ordinary tap water. The agent acts as a competitive complexing agent with the alendronate and produces a soluble metal complex whereas alendronate generally forms an insoluble metal complex leading to the presence of undesirable particulates.

In addition, the presence of an agent, e.g., sodium chloride in an amount of about of 1–8 mg/ml, to adjust the tonicity to the same value of human blood is required to avoid the swelling or shrinkage of erythrocytes upon administration of the intravenous formulation leading to undesirable side effects such as nausea or diarrhea and possibly to associated blood disorders. In general, the tonicity of the formulation matches that of human blood which is in the range of 282 to 288 mOsm/kg, and in general is 285 mOsm/kg, which is equivalent to the osmotic pressure corresponding to a 0.9 % solution of sodium chloride.

The precise dosage by intravenous therapy necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with well-known animal models. In general terms, an effective dose for alendronate in an intravenous liquid formulation is about 1.5 to 3000 µg/kg of body weight and a useful range is about 10 µg/kg to about 200 µg/kg of body weight. A dosage of 2.5–10 mg per person per day introduced over a 2–10 hour period is a useful intravenous dosage regimen.

The intravenous formulation of alendronate can be administered by direct intravenous injection, i.v. bolus, or can be administered by infusion by addition to an appropriate infusion solution such as 0.9% sodium chloride injection or other compatible infusion solution.

An example of an intravenous dosage form of alendronate is as follows:

| General Formulation | |
|---|---|
| Alendronate | 0.5–10.0 mg |
| Sodium Citrate | 5–50 mg |
| Citric Acid | 1–15 mg |
| Sodium Chloride | 1–8 mg |
| Water for Injection (USP) | q.s. 1 mL |

Additional agents such as cosfolvents, preservatives, stabilizers and buffering agents may also be specifically incorporated in the formulation.

The following example is representative of the invention as contemplated by the inventors and should not be construed as being a limitation on the scope or spirit of the invention as claimed.

EXAMPLE

| Specific Formulation | |
|---|---|
| Alendronate (equivalent to 2.5 mg of the acid) | 3.33 mg |
| Sodium Chloride USP Reagent Crystals | 4.91 mg |
| Sodium Citrate USP | 10.3 mg |
| Citric Acid USP | 2.88 mg |
| Water for Injection (USP) | q.s. 1 mL |
| pH = 5.0 | |

Method of Manufacture

Utilizing the above quantities, alendronate is dissolved at room temperature in a previously prepared solution of sodium chloride, citric acid, and sodium citrate in Water for Injection (USP, see page 1636 of the below reference cite)).

The resulting solution is filtered in a sterile environment through a 0.22 micron filter and subdivided into Type 1 glass vials, each with a stopper and aluminum seal.

The vials (contents) are then individually tested according to the applicable government and compendial standards for sterile intravenous solutions. As an example for marketing in the US, the vials would be tested via following protocols found in the US Pharmacopeia. See United States Pharmacopeia/National Formulary for 1995, published by United States Pharmacopeial Convention, Inc., Rockville, Md., copyright 1994, "General Tests and Assays", pages 1648 to 1985:

Sterility: USP method.(page 1686 of above reference cite)

Pyrogen: USP method (page 1718 of above reference cite)

Particulates: USP method (page 1813 of above reference cite).

Tonicity: USP method (page 1813 of above reference cite)

pH: USP method (page 1819 of above reference cite)

COMPARATIVE EXAMPLE

A similar formulation as shown above, in the same proportions but based on 0.1 mg/ml of alendronate, and lacking sodium citrate and citric acid, forms a precipitate after standing for one year at 30 degrees Centigrade.

What is claimed is:

1. An alendronate pharmaceutical composition for intravenous applications; having a pH in the range of 4 to 6 and being isotonic with human blood comprising:

| Alendronate | 0.5–10.0 mg |
|---|---|
| Sodium Citrate | 5–50 mg |
| Citric Acid | 1–15 mg |
| Sodium Chloride | 1–8 mg |
| Water for Injection | q.s. 1 mL. |

2. The pharmaceutical composition of claim 1 having the formula:

| Alendronate | 3.33 mg |
|---|---|
| Sodium Chloride | 4.91 mg |
| Sodium Citrate | 10.29 mg |
| Citric Acid | 2.88 mg |
| Water for Injection | q.s. 1 mL |

3. A method for treating hypercalcemia of malignancy, metastatic bone disease and/or metabolic bone disease in a human patient in need of such treatment comprising the step of administering to said patient a pharmaceutically effective dose of the intravenous alendronate pharmaceutical composition as defined in claim 1.

* * * * *